United States Patent [19]

Aoki et al.

[11] Patent Number: 4,582,928

[45] Date of Patent: Apr. 15, 1986

[54] PROCESS FOR PRODUCING OPTICALLY ACTIVE PHENYLALANINE

[75] Inventors: Shigeru Aoki, Matsudo; Mamoru Katagiri, Saitama; Ryoichi Hasegawa, Yono; Akikazu Mitsunobu, Tokyo; Yasuhisa Tashiro, Yokohama, all of Japan

[73] Assignee: Nippon Kayaku Kabushiki Kaisha, Tokyo, Japan

[21] Appl. No.: 716,400

[22] Filed: Mar. 27, 1985

[30] Foreign Application Priority Data

Apr. 6, 1984 [JP] Japan .................................. 59-67498

[51] Int. Cl.$^4$ .............................................. C07B 19/00
[52] U.S. Cl. .................................. 562/401; 562/402; 562/443
[58] Field of Search ................................ 562/401, 402

[56] References Cited

U.S. PATENT DOCUMENTS 3,492,347 1/1970 Chemerda et al. ................. 562/401
4,224,239 9/1980 Tashiro et al. .................... 562/401 X Primary Examiner—Natalie Trousof
Assistant Examiner—Vera C. Clarke
Attorney, Agent, or Firm—Henry C. Nields

[57] ABSTRACT

This invention relates to a process for producing optically active phenylalanine, characterized by optically resolving DL-phenylalanine.optically active mandelic acid complexes in an aqueous solvent in the presence of an acidic compound having a pKa value of 0.90 to 2.10 and isolating optically active phenylalanine from the obtained optically active phenylalanine.optically active mandelic acid complex.

According to the process of the present invention, it is possible to decrease the amount of a mother liquor of resolution to 1/5 to 1/10 of that when no acidic compound is used and to obtain optically active phenylalanine having an optical purity of as high as 96.5% or above without a step of optical purification when optically active phenylalanine is isolated from the obtained optically active phenylalanine.optically active mandelic acid complex.

15 Claims, No Drawings

PROCESS FOR PRODUCING OPTICALLY ACTIVE PHENYLALANINE

BACKGROUND OF THE INVENTION

A process for optically resolving DL-phenylalanine with the aid of optically active mandelic acid is already known [see Nippon Kagaku Zasshi 92(11), 999–1002 (1971)]. However, when the inventors of the present invention made a follow-up of the well-known process, it was found that the process was extremely disadvantageous for industrial practice because the solubility of the phenylalanine.mandelic acid complex in water was extremely low (2.6% in terms of phenylalanine), the optical purity of the resolved optically active phenylalanine was as high as about 80% unsatisfactorily, even after considerations of various conditions and, because of the low initial concentration as mentioned above, the ratio of the obtained optically active phenylalanine.mandelic acid complex to the mother liquor of resolution was extremely low.

SUMMARY OF THE INVENTION

After studies to eliminate the above-mentioned drawbacks, the inventors of the present invention have found that the DL-phenylalanine.optically active mandelic acid complexes can be optically resolved without decomposing in an aqueous solvent in the presence of an acidic compound having a pKa value of 0.90 to 2.10; that the amount of a mother liquor of resolution can be decreased to 1/5 to 1/10 of that when no acidic compound is used; that optically active phenylalanine having an optical purity of as high as 96.5% or above can be obtained without a step of optical purification when optically active phenylalanine is isolated from the obtained optically active phenylalanine.optically active mandelic acid complex; and that the degree of resolution can be improved markedly when an aldehyde is present during the optical resolution.

The present invention has been accomplished on the basis of the above findings.

DETAILED DESCRIPTION OF THE INVENTION

The process of the present invention can be practiced for example, as follows. DL-Phenylalanine and optically active mandelic acid are dissolved in an aqueous solvent containing an acidic compound having a pKa value of 0.90 to 2.10 to form DL-phenylalanine.optically active mandelic acid complexes; this solution is cooled and, if required, concentrated to crystallize the difficultly soluble complex selectively, the mixture is subjected to solid/liquid separation; the obtained optically active phenylalanine.optically active mandelic acid complex is decomposed by means of, for example, ion exchange resin treatment or neutralization; and the mandelic acid is removed to obtain optically active phenylalanine.

Examples of the acidic compounds having a pKa value of 0.90 to 2.10 used in this invention include inorganic compounds such as sulfamic acid, sulfurous acid, sulfuric acid, bisulfates, thiosulfuric acid, hypophosphorous acid, phosphorous acid, and chlorous acid, among which sulfuric acid, bisulfates, sulfamic acid, etc., are desirable. The bisulfates are not particularly limited, and examples of them include bisulfates of metals such as lithium, sodium, and potassium, that of ammonia, those of amines such as methylamine and aniline, and those of amino acids such as phenylalanine and glycine, among which ammonium bisulfate, sodium bisulfate, potassium bisulfate, and bisulfates of amino acids have a particular industrial importance. A mixture of them can of course be used. Any of these may be formed in the system of resolution for use. For example, sulfuric acid is reacted with an equimolar amount of sodium hydroxide or Glauber's salt in water to form sodium bisulfate, which is used as such in this invention.

The amount of the acidic compound used is such that the compound is present in an amount, for example, less than twice, by mole, desirably 0.2 to 1.6 times, by mole, more desirably 0.6 to 1.2 times, by mole, the amount of DL-phenylalanine in the DL-phenylalanine optically active mandelic acid complexes, or the sum of this amount and the amount of excess DL-phenylalanine if present in addition to that contained in said complex (hereinafter referred to simply as "the amount of DL-phenylalanine"). When the acidic compound is sulfuric acid, it is used in an amount less than once, by mole, desirably 0.1 to 0.8 time, by mole, more desirably 0.3 to 0.6 time, by mole, that of DL-phenylalanine.

Any solvents may be used without particular limitation so long as they can dissolve both of phenylalanine and mandelic acid and allow formation of a complex between them, and water, hydrous alcohol, etc., can be mentioned.

It is preferred that the concentration of the DL-phenylalanine.optically active mandelic acid complexes in a solvent is 10 to 70 w/v %, desirably 25 to 45 w/v %.

The DL-phenylalanine.optically active mandelic acid complex can be obtained by dissolving DL-phenylalanine and optically active mandelic acid in an aqueous solvent. In the present invention, this solution may be used as such or the complex isolated therefrom may be used.

When using the solution of DL-phenylalanine and optically active mandelic acid as such in optical resolution, the ratio of mandelic acid to phenylalanine in the preparation of the solution is at least 0.1 by equivalent, desirably 0.2 to 4 by equivalent, more desirably 0.4 to 2 by equivalent, but it is determined suitably according to the amount of an acidic compound added.

Although the temperature in the preparation of the solution of the complexes is not particularly limited so long as it is 0° C. or above, it is desirably in the range from 50° C. to the boiling point of a solvent.

Although the temperature of crystallization is not particularly limited so long as it is below the boiling point of a solvent used, it is desirably in the range from 0° to 60° C.

The agitation time during crystallization is not particularly limited, and an agitation time of, for example, about 30 minutes is sufficient.

Although the addition of seed crystals is not necessary for the crystallization of the optically active complex, a small amount of seed crystals may be added without any objection in order to accelerate crystallization. Further, the use of an aldehyde in crystallization is desirable because the degree of resolution can be increased markedly.

The aldehydes which can be mentioned include aromatic aldehydes and aliphatic aldehydes such as acetaldehyde, among which aromatic aldehydes which may be substituted with a group or groups such as hydroxy, lower alkoxy, nitro, or halogen are desirable. Examples of them include benzaldehydes such as benzaldehyde, salicylaldehyde, m-hydroxybenzaldehyde, p-hydroxybenzaldehyde, o-nitrobenzaldehyde, p-nitrobenzaldehyde, 5-nitrosalicylaldehyde, anisaldehyde, vanillin, chlorosalicylaldehyde, and bromosalicylaldehyde; and β-naphthol-α-aldehyde. These aldehydes are used preferably in an amount 0.02 to 3 times, by mole, desirably 0.05 to 1 time, by mole, more desirably 0.1 to 0.5 times, by mole, that of DL-phenylalanine.

Although the agitation time for crystallization in the presence of an aldehyde is not particularly limited, a longer time, for example, 3 hours or longer, desirably 7 to 72 hours, is desirable for the purpose of increasing the yields of the difficultly soluble complex and of obtaining a crystal containing optically active phenylalanine with a high optical purity.

The isolation of optically active phenylalanine from the obtained optically active complex can be effected by a well-known method. For example, the isolation can be readily performed by neutralizing an aqueous solution of the optically active phenylalanine.optically active mandelic acid complex with a caustic alkali to precipitate the desired optically active phenylalanine and filtering the precipitate, or by passing an aqueous solution of the optically active complex through a column of a strongly acidic ion exchange resin, washing the column with water, eluting the column with ammonia water, concentrating the eluate and filtering the precipitated crystals.

The above-mentioned production process of the optically active phenylalanine can be practiced more efficiently by using an aldehyde, adding DL-phenylalanine and optically active mandelic acid to a solution which has been subjected to a resolving operation, dissolving the compounds by heating to obtain a supersaturated solution and repeating the above resolving procedure.

The L-isomer of the optically active phenylalanine obtained in the present invention is useful as a component of an amino acid transfusion or a raw material for sweetening agents, and the D-isomer is useful as a raw material for medicines or the like.

The present invention will now be described in detail with reference to examples.

EXAMPLE 1

16.5 g of 95% sulfuric acid was added to 200 ml of water. 66.1 g of DL-phenylalanine and 73.2 g of L-mandelic acid were added to the solution. The mixture was heated to 75° C. to form a solution. This solution was cooled slowly and, when it was cooled to 69° C., 0.27 g of an L-phenylalanine.L-mandelic acid complex was added as seed crystals. When the solution was cooled to 30° C. after about 2 hours, the precipitated crystals were separated by filtration and washed with 50 ml of water to obtain 53.6 g (42.44 g of dried crystals) of wet crystals of L-phenylalanine.L-mandelic acid complex (phenylalanine to mandelic acid molar ratio of 1:1). The degree of resolution was 33.2%.

The resolved crystals were suspended in 95 g of water, and the suspension was neutralized with 18 g of a 30% aqueous sodium hydroxide solution at 30° to 50° C. The precipitated L-phenylanine was filtered at room temperature, washed with 20 ml of water and dried to obtain 18.7 g of L-phenylalanine.

specific rotation $[\alpha]_D^{20} = -34.2°$ (C=2.0 in H$_2$O)
optical purity: 99.4%

EXAMPLE 2

41.3 g of 95% sulfuric acid was added to 150 ml of water. 53.3 g of 30% NaOH was added dropwise to the solution with stirring at 30 to 50° C. over a period of 0.5 hour to prepare an aqueous NaHSO$_4$ solution. 66.1 g of DL-phenylalanine and 73.2 g of L-mandelic acid were added thereto and the mixture was heated to 75° C. to form a uniform solution. This solution was cooled slowly and, when it was cooled to 67° C., 0.25 g of an L-phenylalanine.L-mandelic acid complex was added as seed crystals and the solution was further cooled. After 5.5 hours, the formed crystals were filtered at 25° C., washed with 70 ml of water, and dried to obtain 51.1 g of an L-phenylalanine.L-mandelic acid complex (phenylalanine to mandelic acid molar ratio of 1:1). The degree of resolution was 34.2%.

19.0 g of the obtained complex was dissolved in 950 ml of water, and the solution was passed through a column of 100 ml of Dowex 50W X-4 (H-form). The column was washed throughly with water and eluted with 500 ml of 1N ammonia water. 1,000 ml of the eluate was concentrated in vacuum and crystallized by the addition of methanol. The precipitated crystals were filtered, washed with cold water and dried to obtain 9.70 g of L-phenylalanine.

specific rotation $[\alpha]_D^{20} = -33.50°$ (C=2 in H$_2$O)
optical purity: 97.4%

EXAMPLE 3

This example was carried out in the same manner as in Example 1 except 46 g of NH$_4$HSO$_4$ was used instead of sulfuric acid. The concentration of DL-phenylalanine was 17.2 %, and the molar ratios of NH$_4$HSO$_4$ and L-mandelic acid to DL-phenylalanine were 1.0 and 1.2, respectively. The mixture was heated to 77° C. to form a uniform solution. This solution was cooled slowly and, when the solution was cooled to 71° C., 0.22 g of an L-phenylalanine.L-mandelic acid complex was added as seed crystals. The solution was further cooled to 23° C. over a period of 3 hours, and the formed crystals of an L-phenylalanine.L-mandelic acid complex (phenylalanine to mandelic acid molar ratio of 1:1) were filtered. The crystals were washed with 55 ml of water and dried. The yield of the product after drying was 52.87 g. The degree of resolution was 41 %.

The obtained complex was treated in the same manner as in Example 1 to obtain L-phenylalanine.

specific rotation $[\alpha]_D^{20} = -33.9°$ (C=2 in H$_2$O)
optical purity: 98.5%

EXAMPLE 4

This example was carried out in the same manner as in Example 3 except that 55.2 g (1.2 times, by mole, the amount of DL-phenylalanine) of NH$_4$HSO$_4$ and 140 ml of water were added. 49.44 g of an L-phenylalanine.L-mandelic acid complex (phenylalanine to mandelic acid molar ratio of 1:2) was obtained. The degree of resolution was 26.2%.

The obtained complex was treated with a strongly acidic ion exchange resin in the same manner as in Example 2 to obtain L-phenylalanine.

specific rotation $[\alpha]_D^{20} = -34.0°$ (C=2 in H$_2$O)
optical purity: 98.8%

EXAMPLE 5

This example was carried out in the same manner as in Example 1 except that 43.8 g of L-mandelic acid and 160 ml of water were used. 40.16 g of an L-phenylalanine.L-mandelic acid complex (phenylalanine to mandelic acid molar ratio of 1:1) was obtained. The degree of resolution was 30.7%.

The obtained complex was treated in the same manner as in Example 1 to obtain L-phenylalanine.
specific rotation $[\alpha]_D^{20} = -33.4°$ (C=2 in H$_2$O)
optical purity: 97.1%

EXAMPLE 6

27.2 g of sulfamic acid was added to 200 ml of water. 66.1 g of DL-phenylalanine and 73.2 g of L-mandelic acid were added to the solution. The mixture was heated to 76° C. to form a solution. This solution was cooled slowly and, when the solution was cooled to 68° C., 0.27 g of an L-phenylalanine.L-mandelic acid complex was added as seed crystals. When the solution was cooled to 35° C. after about 0.5 hour, the precipitated crystals were filtered, washed with 50 ml of water and dried to obtain 42.28 g of an L-phenylalanine.L-mandelic acid complex (phenylalanine to mandelic acid molar ratio of 1:1). The degree of resolution was 32.6%.

The obtained complex was treated in the same manner as in Example 2 to obtain L-phenylalanine.
specific rotation $[\alpha]_D^{20} = -33.67°$ (C=2.0 in H$_2$O)
optical purity: 97.9%

EXAMPLE 7

50.4 g of sulfamic acid was added to 200 ml of water. 66.1 g of DL-phenylalanine and 73.2 g of mandelic acid were added to the solution, and the mixture was heated to 76° C. to form a solution. This solution was cooled slowly and, when it was cooled to 55° C., 0.2 g of an L-phenylalanine.L-mandelic acid complex was added as seed crystals. When the solution was cooled to 30° C. after about 2 hours, the precipitated crystals were filtered, washed with 50 ml of water and dried to obtain 38.76 g of an L-phenylalanine.L-mandelic acid complex (phenylalanine to mandelic acid molar ratio of 1:1.59). The degree of resolution was 24%.

The obtained complex was treated in the same manner as in Example 2 to obtain L-phenylalanine.
specific rotation $[\alpha]_D^{20} = -33.96°$ (C=2 in H$_2$O)
optical purity: 98.7%

EXAMPLE 8

16.5 g of 95% sulfuric acid was added to 187.5 g of water. 66.1 g of DL-phenylalanine, 73.2 g of L-mandelic acid and 12.5 g of salicylaldehyde were added to the solution, and the mixture was heated to 75° C. to form a solution.

This solution was cooled slowly and, when it was cooled to 70° C., 0.03 g of an L-phenylalanine.L-mandelic acid complex was added. The solution was cooled to 60° C., agitated slowly at the same temperature for 8 hours and cooled to 30° C. over a period of 1 hour. The precipitated crystals were filtered at 30° C., washed with 70 g of water and dried to obtain 65.6 g of an L-phenylalanine.L-mandelic acid complex (phenylalanine to mandelic acid molar ratio of 1:1). The degree of resolution was 52.1 %. 10.0 g of the crystals were dissolved in 60.0 ml of water by heating, and the solution was neutralized to a pH of 6.0 by the addition of 6.0 g of 20 % sodium hydroxide. The precipitated crystals were filtered, washed with water and dried to obtain 3.0 g of L-phenylalanine.
specific rotation $[\alpha]_D^{20} = -34.0°$ (C=2 in H$_2$O)
optical purity: 98.8%

EXAMPLE 9

To the filtrate obtained in Example 8 were added 35.0 g of DL-phenylalanine, 33.0 g of L-mandelic acid, 2.3 g of salicylaldehyde, and 13.0 g of water. The mixture was heated to form a solution. When this solution was cooled to 50° C. after 1 hour, 0.03 g of an L-phenylalanine.L-mandelic acid complex was added thereto as seed crystals. The solution was agitated slowly for 36 hours at the same temperature, and then cooled to 30° C. over a period of 1 hour. Thereafter, the solution was treated in the same manner as in Example 8 to obtain 3.1 g of L-phenylalanine.
specific rotation $[\alpha]_D^{20} = -33.9°$ (C=2 in H$_2$O)
optical purity: 98.5%
the degree of resolution: 52.8%

EXAMPLE 10

39.5 g of 95% sulfuric acid was added to 141.0 ml of water. 51.1 g of a 30% NaOH solution was added to the solution with stirring to prepare an aqueous NaHSO$_4$ solution. To this solution were added 66.1 g of DL-phenylalanine, 73.2 g of L-mandelic acid, and 9.8 g of salicylaldehyde, and the mixture was heated to 75° C. to form a solution. This solution was cooled and, when it was cooled to 69° C., 0.05 g of an L-phenylalanine.L-mandelic acid complex was added as seed crystals. The solution was further cooled, agitated slowly at 55° C. for 10 hours, and further cooled to 30° C. The precipitated crystals were filtered, washed with 70 ml of water and dried to obtain 63.7 g of an L-phenylalanine.L-mandelic acid complex (phenylalanine to mandelic acid molar ratio of 1:1). The degree of resolution was 50.3%.

10.0 g of the resolved crystals were treated in the same manner as in Example 8 to obtain 3.0 g of L-phenylalanine.
specific rotation $[\alpha]_D^{20} = -33.8°$ (C=2 in H$_2$O)
optical purity: 98.3%

EXAMPLE 11

46 g of NH$_4$HSO$_4$ was added to 185.2 g of water. 66.1 g of DL-phenylalanine, 73.2 g of L-mandelic acid and 14.8 g of salicylaldehyde were added to the solution. The mixture was heated to 75° C. to form a solution. This solution was cooled to 60° C. and 0.03 g of an L-phenylalanine.L-mandelic acid complex was added thereto. The solution was agitated slowly at the same temperature for 12 hours. The precipitated crystals were filtered, washed with 70 ml of water and dried to obtain 66.9 g of an L-phenylalanine.L-mandelic acid complex (phenylalanine to L-mandelic acid molar ratio of 1:1). The degree of resolution was 52.4%. 10.0 g of the crystals were treated in the same manner as in Example 8 to obtain 3.0 g of L-phenylalanine.
specific rotation $[\alpha]_D^{20} = -33.5°$ (C=2 in H$_2$O)
optical purity: 97.4%

EXAMPLE 12

14.45 g of 95% H$_2$SO$_4$ was added to 141.6 g of water. 66.1 g of DL-phenylalanine, 73.2 g of L-mandelic acid and 8.4 g of o-anisaldehyde were added to the solution, ahd the mixture was heated to 75° C. to form a solution. This solution was cooled to 60° C. and 0.03 g of an L-phenylalanine.L-mandelic acid complex was added thereto. The solution was agitated slowly at the same temperature for 8 hours and further cooled to 30° C. The precipitated crystals were filtered, washed with 70 ml of water and dried to obtain 65.2 g of an L- phenylalanine.L-mandelic acid complex (phenylalanine to mandelic acid molar ratio of 1:1). The degree of resolution was 51.9%. 10.0 g of the crystals were treated in the same manner as in Example 8 to obtain 3.1 g of L-phenylalanine.

specific rotation $[\alpha]_D^{20} = -34.1°$ (C=2 in H$_2$O)
optical purity: 99.1%

Referential Example 1

This example was carried out by using quite the same formulation as in Example 1 except that no sulfuric acid was used. The mixture was heated to 80 to 90° C. to dissolve the reactants, but no uniform solution could be obtained. Therefore, water was added slowly to the mixture. After 1,550 ml of water had been added, the reactants could be dissolved. The obtained solution was cooled slowly in the same manner as in Example 1. During the cooling, 0.27 g of an L-phenylalanine.L-mandelic acid complex was added as seed crystals, and the solution was further cooled to 30° C. after about 3 hours. The precipitated crystals were filtered, washed with water and dried to obtain 52.94 g of an L-phenylalanine.L-mandelic acid complex (phenylalanine to mandelic acid molar ratio of 1:1). The degree of resolution was 35.1%.

This complex was treated in quite the same manner as in Example 2 to obtain 21.2 g of L-phenylalanine.

specific rotation $[\alpha]_D^{20} = -28.9°$ (C=2 in H$_2$O)
optical purity: 84.10%

What is claimed is:

1. A process for producing optically active phenylalanine, which comprises optically resolving DL-phenylalanine.optically active mandelic acid complexes in an aqueous solvent in the presence of an acidic compound having a pKa value of 0.90 to 2.10, wherein the amount of the acidic compound is less than twice, by mole, the amount of DL-phenylalanine; except that when the acidic compound is sulfuric acid the amount of the acidic compound is less than once; and isolating optically active phenylalanine from the obtained optically active phenylalanine.optically active mandelic acid complex.

2. A process according to claim 1, wherein said acidic compound is selected from the group consisting of sulfamic acid, sulfurous acid, bisulfates, thiosulfuric acid, hypophosphorous acid, phosphorous acid and chlorous acid, said compound being used in an amount less than twice, by mole, that of DL-phenylalanine.

3. A process according to claim 1, wherein said acidic compound is selected from the group consisting of sulfamic acid and bisulfates.

4. A process according to claim 2, wherein said bisulfate is selected from the group consisting of bisulfates of alkali metals, ammonium, amines, and amino acids.

5. A process according to claim 3, wherein said bisulfate is selected from the group consisting of ammonium bisulfate, sodium bisulfate, potassium bisulfate, a bisulfate of phenylalanine and a bisulfate of glycine.

6. A process according to claim 2, wherein said acidic compound is used in an amount 0.6 to 1.2 times, by mole, that of DL-phenylalanine.

7. A process according to claim 1, wherein said acidic compound is sulfuric acid and used in an amount less than once, by mole, that of DL-phenylalanine.

8. A process according to claim 7, wherein sulfuric acid is used in an amount 0.3 to 0.6 time, by mole, that of DL-phenylalanine.

9. A process according to claim 1, wherein said solvent is water.

10. A process according to claim 1, wherein the concentration of said DL-phenylalanine.optically active mandelic acid complexes in a solvent is 25 to 45 w/v %.

11. A process according to claim 1, wherein the optical resolution is carried out in the presence of an aldehyde in an amount 0.02–3 times, by mole, the amount of DL-phenylalanine.

12. A process according to claim 11, wherein said aldehyde is an aromatic aldehyde which may be substituted with hydroxy, lower alkoxy, nitro, or halogen.

13. A process according to claim 11, wherein said aldehyde is selected from the group consisting of benzaldehyde, salicylaldehyde, m-hydroxybenzaldehyde, p-hydroxybenzaldehyde, o-nitrobenzaldehyde, p-nitrobenzaldehyde, 5-nitrosalicylaldehyde, anisaldehyde, vanillin, chlorosalicylaldehyde, bromosalicylaldehyde, and β-naphthol-α-aldehyde.

14. A process according to claim 11, wherein said aldehyde is used in an amount 0.1 to 0.5 times, by mole, that of DL-phenylalanine.

15. A process for producing optically active phenylalanine, which comprises crystallizing an optically active phenylalanine.optically active mandelic acid complex from a 25–45 w/v % aqueous solution of DL-phenylalanine.optically active mandelic acid complexes in the presence of sulfuric acid in an amount 0.3 to 0.6 time, by mole, that of DL-phenylalanine and salicylaldehyde in an amount 0.1 to 0.5 times, by mole, that of DL-phenylalanine, and isolating optically active phenylalanine from the crystallized complex.

* * * * *